United States Patent
Krueger et al.

(10) Patent No.: US 12,121,877 B2
(45) Date of Patent: Oct. 22, 2024

(54) METHOD FOR THE PRODUCTION OF SUPERABSORBERS

(71) Applicant: BASF SE, Ludwigshafen (DE)

(72) Inventors: Marco Krueger, Ludwigshafen (DE); Ruediger Funk, Ludwigshafen (DE); Thomas Pfeiffer, Ludwigshafen (DE); Karl Possemiers, Antwerp (BE); Juergen Schroeder, Ludwigshafen (DE); Matthias Weismantel, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 939 days.

(21) Appl. No.: 17/258,931

(22) PCT Filed: Jul. 15, 2019

(86) PCT No.: PCT/EP2019/068942
§ 371 (c)(1),
(2) Date: Jan. 8, 2021

(87) PCT Pub. No.: WO2020/020675
PCT Pub. Date: Jan. 30, 2020

(65) Prior Publication Data
US 2021/0291145 A1  Sep. 23, 2021

(30) Foreign Application Priority Data
Jul. 24, 2018 (EP) .................... 18185245

(51) Int. Cl.
| | |
|---|---|
| *B01J 20/26* | (2006.01) |
| *A61L 15/26* | (2006.01) |
| *A61L 15/60* | (2006.01) |
| *B01J 20/28* | (2006.01) |
| *B01J 20/30* | (2006.01) |
| *C08F 20/06* | (2006.01) |
| *C08J 3/24* | (2006.01) |

(52) U.S. Cl.
CPC ............ *B01J 20/267* (2013.01); *A61L 15/26* (2013.01); *A61L 15/60* (2013.01); *B01J 20/28016* (2013.01); *B01J 20/3085* (2013.01); *C08F 20/06* (2013.01); *C08J 3/245* (2013.01); *C08F 2810/20* (2013.01)

(58) Field of Classification Search
CPC ........ C08F 20/04; C08F 20/06; C08F 120/04; C08F 120/06; C08F 220/04; C08F 220/06
See application file for complete search history.

(56) References Cited

U.S. PATENT DOCUMENTS

| | | | |
|---|---|---|---|
| 2008/0242816 A1* | 10/2008 | Weismantel | .......... C07C 51/412 422/68.1 |
| 2011/0313113 A1 | 12/2011 | Sakamoto et al. | |
| 2012/0258851 A1 | 10/2012 | Nakatsuru et al. | |
| 2014/0031473 A1* | 1/2014 | Nogi | ....................... C08F 20/06 525/383 |

FOREIGN PATENT DOCUMENTS

| | | |
|---|---|---|
| DE | 102005042604 A1 | 3/2007 |
| DE | 102005042605 A1 | 3/2007 |
| DE | 102005042606 A1 | 3/2007 |

OTHER PUBLICATIONS

Graham, et al., "Chapter 3—Commercial processes for the manufacture of superabsorbent polymer" Modern Superabsorbent Polymer Technology, Ed. Buchholz, 1998, pp. 71 to 117.
International Application No. PCT/EP2019/068942, International Search Report, mailed Oct. 15, 2019.

* cited by examiner

*Primary Examiner* — John M Cooney
*Assistant Examiner* — Jeffrey S Lenihan
(74) *Attorney, Agent, or Firm* — Element IP, PLC

(57) ABSTRACT

A process for producing superabsorbent particles by polymerizing a monomer solution or suspension, comprising the steps of continuously preneutralizing a monomer while cooling and partly recycling the preneutralized monomer into the preneutralization, continuously heating the preneutralized monomer by means of a heat exchanger and continuously postneutralizing the heated monomer, wherein the monomer solution or suspension prior to entry into the polymerization reactor is at a temperature of 70 to 99° C. and the temperature of the heating medium used in the heat exchanger is less than 160° C.

15 Claims, No Drawings

METHOD FOR THE PRODUCTION OF SUPERABSORBERS

CROSS-REFERENCE TO RELATED APPLICATIONS

This is the U.S. national phase of International Application No. PCT/EP2019/068942, filed Jul. 15, 2019, which claims the benefit of European Patent Application No. 18185245.0, filed on Jul. 24, 2018.

The present invention relates to a process for producing superabsorbent particles by polymerizing a monomer solution or suspension, comprising the steps of continuously preneutralizing a monomer while cooling and partly recycling the preneutralized monomer into the preneutralization, continuously heating the preneutralized monomer by means of a heat exchanger and continuously postneutralizing the heated monomer, wherein the monomer solution or suspension prior to entry into the polymerization reactor is at a temperature of 70 to 99° C. and the temperature of the heating medium used in the heat exchanger is less than 160° C.

Superabsorbents are used to produce diapers, tampons, sanitary napkins and other hygiene articles, but also as water-retaining agents in market gardening. Superabsorbents are also referred to as water-absorbing polymers.

The production of superabsorbents is described in the monograph "Modern Superabsorbent Polymer Technology", F. L. Buchholz and A. T. Graham, Wiley-VCH, 1998, pages 71 to 103.

The properties of the superabsorbents can be adjusted, for example, via the amount of crosslinker used. With increasing amount of crosslinker, the centrifuge retention capacity (CRC) falls and the absorption under a pressure of 21.0 g/cm$^2$ (AUL0.3 psi) passes through a maximum.

To improve the performance properties, for example gel bed permeability (GBP) and absorption under a pressure of 49.2 g/cm$^2$ (AUL0.7 psi), superabsorbent particles are generally surface postcrosslinked. This increases the level of crosslinking of the particle surface, which can at least partly decouple the absorption under a pressure of 49.2 g/cm$^2$ (AUL0.7 psi) and the centrifuge retention capacity (CRC). This surface postcrosslinking can be performed in the aqueous gel phase. Preferably, however, dried, ground and sieved polymer particles (base polymer) are surface coated with a surface postcrosslinker and thermally surface postcrosslinked. Crosslinkers suitable for that purpose are compounds which can form covalent bonds with at least two carboxylate groups of the polymer particles.

US 2011/0313113 and US 2012/0258851 disclose the polymerization of monomer solutions with dispersed gas bubbles. One means of generating the dispersed gas bubbles that is mentioned is starting the polymerization at very high temperatures.

It was an object of the present invention to provide an improved process for producing superabsorbents, especially a reduction in the dwell time of the monomer solution at very high temperatures prior to entry into the polymerization reactor, with simultaneously very high temperature of the monomer solution on entry into the polymerization reactor.

The object was achieved by a process for producing superabsorbents by polymerizing a monomer solution or suspension comprising
a) at least one ethylenically unsaturated monomer which bears acid groups and is at least partly neutralized,
b) at least one crosslinker,
c) at least one initiator,
d) optionally one or more ethylenically unsaturated monomers copolymerizable with the monomers mentioned under a) and
e) optionally one or more water-soluble polymers, comprising the steps of
  i) continuously preneutralizing the monomer while cooling and partly recycling the preneutralized monomer into the preneutralization,
  ii) continuously heating the preneutralized monomer from step i) by means of a heat exchanger,
  iii) continuously postneutralizing the heated monomer from step ii),
  iv) adding the crosslinker to the monomer solution from step iii) and
  v) adding the initiator to the monomer solution from step iv),
wherein the monomer solution or suspension is at a temperature of 70 to 99° C. prior to entry into the polymerization reactor and the temperature of the heating medium used in the heat exchanger in step ii) is less than 160° C.

The preneutralized monomer is cooled in step i) to a temperature of preferably less than 45° C., more preferably less than 40° C., most preferably less than 35° C. Lower temperatures lower the tendency to polymerization.

The preneutralized monomer is recycled into step i) preferably to an extent of 40% to 98%, more preferably to an extent of 60% to 95%, most preferably to an extent of 80% to 90%. The recycling results in dilution of fresh monomer with preneutralized monomer solution and avoids overheating.

A suitable process for continuous preneutralization with recycling is described, for example, in WO 2007/028751 A2.

The temperature of the heating medium in step ii) is preferably less than 140° C., more preferably less than 120° C., most preferably less than 110° C.

In the postneutralization in step iii), the neutralization level of monomer a) is increased by preferably 5 to 45 mol %, more preferably 10 to 35 mol %, most preferably 15 to 25 mol %.

A suitable process for continuous postneutralization is described, for example, in WO 2007/028747 A1.

The present invention is based on the finding that the dwell time of the monomer solution at very high temperatures prior to entry into the polymerization reactor can be lowered by a suitable reaction regime, and hence the tendency to polymerization prior to entry into the polymerization reactor.

In a particularly preferred embodiment of the present invention, a chelating agent is added to the monomer solution prior to step iii).

In a very particularly preferred embodiment of the present invention, a chelating agent is added to the monomer solution prior to step ii).

The production of the superabsorbents is described in detail hereinafter:

The superabsorbents are produced by polymerizing a monomer solution or suspension, and are typically water-insoluble.

The monomers a) are preferably water-soluble, i.e. their solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 02/055469 A1, WO 03/078378 A1 and WO 2004/035514 A1. A suitable monomer a) is, for example, an acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 03/104299 A1, WO 03/104300 A1, WO 03/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 02/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or propoxylated glycerols which have been esterified with acrylic acid or methacrylic acid to give di- or triacrylates, as described, for example, in WO 03/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05% to 1.5% by weight, more preferably 0.1% to 0.8% by weight and most preferably 0.15% to 0.5% by weight, calculated in each case on the basis of the total amount of monomer a) used. With rising crosslinker content, centrifuge retention capacity (CRC) falls and the absorption under a pressure of 21.0 $g/cm^2$ passes through a maximum.

Initiators c) used may be all compounds which generate free radicals under the polymerization conditions, for example thermal initiators, redox initiators or photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is preferably the disodium salt of 2-hydroxy-2-sulfonatoacetic acid or a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methyl cellulose or hydroxyethyl cellulose, gelatin, polyglycols or polyacrylic acids, preferably starch, starch derivatives and modified cellulose.

Typically, an aqueous monomer solution is used. The water content of the monomer solution is preferably from 40% to 75% by weight, more preferably from 45% to 70% by weight and most preferably from 50% to 65% by weight. It is also possible to use monomer suspensions, i.e. monomer solutions with monomer a) over and above the solubility, for example sodium acrylate. As the water content rises, the energy expenditure in the subsequent drying rises and, as the water content falls, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors for the polymerization are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on the belt is described, for example, in DE 38 25 366 A1 and U.S. Pat. No. 6,241,928. Polymerization in a belt reactor forms a polymer gel which has to be comminuted, for example in an extruder or kneader.

To improve the drying properties, the comminuted polymer gel obtained by means of a kneader can additionally be extruded.

The acid groups of the resulting polymer gels have typically been partly neutralized. Neutralization is preferably carried out at the monomer stage. This is typically accomplished by mixing in the neutralizing agent as an aqueous solution or else preferably as a solid. The degree of neutralization is preferably from 25 to 85 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof. Solid carbonates and hydrogencarbonates can also be introduced here in encapsulated form, preferably into the monomer solution directly prior to the polymerization, into the polymer gel during or after the polymerization and prior to the drying thereof. The encapsulation is effected by coating of the surface with an insoluble or only gradually soluble material (for example by means of film-forming polymers, of inert inorganic materials or of fusible organic materials) which delays the dissolution and reaction of the solid carbonate or hydrogencarbonate to such a degree that carbon dioxide is not released until during the drying and the superabsorbent formed has high internal porosity.

Optionally, a surfactant can be added to the monomer solution before or during the polymerization and the monomer solution can then be foamed before or during the polymerization with an inert gas or water vapor or by vigorous stirring. The surfactant may be anionic, cationic, zwitterionic or else nonionic. Preference is given to using a skin-friendly surfactant.

The polymer gel is then typically dried with an air circulation belt drier until the residual moisture content is preferably 0.5 to 10% by weight, more preferably 1 to 6% by weight and most preferably 1.5 to 4% by weight, the residual moisture content being determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the polymer gel before the drying is preferably from 25% to 90% by weight, more preferably from 35% to 70% by weight, most preferably from 40% to 60% by weight. Subsequently, the dried polymer gel is crushed and optionally coarsely comminuted.

Thereafter, the dried polymer gel is typically ground and classified, and the apparatus used for grinding may typically be single- or multistage roll mills, preferably two- or three-stage roll mills, pin mills, hammer mills or vibratory mills.

The average particle size of the polymer particles removed as the product fraction is preferably from 150 to 850 µm, more preferably from 250 to 600 µm, very particularly from 300 to 500 µm. The average particle size of the product fraction may be determined by means of EDANA recommended test method No. WSP 220.2-05 "Particle Size Distribution", where the proportions by mass of the screen fractions are plotted in cumulated form and the average particle size is determined graphically. The average particle size here is the value of the mesh size which arises for a cumulative 50% by weight.

The proportion of polymer particles having a particle size of greater than 150 µm is preferably at least 90% by weight, more preferably at least 95% by weight, most preferably at least 98% by weight.

Polymer particles with too small a particle size lower the gel bed permeability (GBP). The proportion of excessively small polymer particles ("fines") should therefore be small.

Excessively small polymer particles are therefore typically removed and recycled into the process, preferably before, during or immediately after the polymerization, i.e. prior to the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

If a kneading reactor is used for polymerization, the excessively small polymer particles are preferably added during the last third of the polymerization. However, it is also possible to incorporate the excessively small polymer particles into the polymer gel in a kneader or extruder connected downstream of the polymerization reactor.

If the excessively small polymer particles are added at a very early stage, for example actually to the monomer solution, this lowers the centrifuge retention capacity (CRC) of the resulting polymer particles. However, this can be compensated, for example, by adjusting the amount of crosslinker b) used.

The proportion of polymer particles having a particle size of at most 850 µm is preferably at least 90% by weight, more preferably at least 95% by weight, most preferably at least 98% by weight.

The proportion of polymer particles having a particle size of at most 600 µm is preferably at least 90% by weight, more preferably at least 95% by weight, most preferably at least 98% by weight.

Polymer particles of excessively large particle size lower the swell rate. The proportion of excessively large polymer particles should therefore likewise be low. Excessively large polymer particles are therefore typically removed and recycled into the grinding.

To further improve the properties, the polymer particles can be thermally surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amido acetals in DE 103 34 584 A1, oxetanes and cyclic ureas in EP 1 199 327 A2 and morpholine-2,3-dione and derivatives thereof in WO 03/031482 A1. Preferred surface postcrosslinkers are ethylene carbonate, ethylene glycol diglycidyl ether, reaction products of polyamides with epichlorohydrin and mixtures of propylene glycol and butane-1,4-diol.

Very particularly preferred surface postcrosslinkers are 2-hydroxyethyl-2-oxazolidinone, 2-oxazolidinone and propane-1,3-diol.

In addition, it is also possible to use surface postcrosslinkers which comprise additional polymerizable ethylenically unsaturated groups, as described in DE 37 13 601 A1.

The amount of surface postcrosslinker is preferably 0.001% to 3% by weight, more preferably 0.02% to 1% by weight and most preferably 0.05% to 0.2% by weight, based in each case on the polymer particles.

The surface postcrosslinking is typically performed in such a way that a solution of the surface postcrosslinker is sprayed onto the dried polymer particles. After the spray application, the polymer particles coated with surface postcrosslinker are surface postcrosslinked and dried, and the surface postcrosslinking reaction can take place both before and during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers have a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting characteristics and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The surface postcrosslinking is preferably performed in contact dryers, more preferably paddle dryers, most preferably disk dryers. Suitable dryers are, for example, Hosokawa Bepex® Horizontal Paddle Dryer (Hosokawa Micron GmbH; Leingarten; Germany), Hosokawa Bepex® Disk Dryer (Hosokawa Micron GmbH; Leingarten; Germany), Holo-Flite® dryers (Metso Minerals Industries Inc.; Danville; USA) and Nara Paddle Dryer (NARA Machinery Europe; Frechen; Germany). Moreover, fluidized bed dryers may also be used.

The surface postcrosslinking can be effected in the mixer itself, by heating the jacket or blowing in warm air. Equally suitable is a downstream dryer, for example a tray dryer, a rotary tube oven or a heatable screw. It is particularly advantageous to effect mixing and thermal surface postcrosslinking in a fluidized bed dryer.

Preferred reaction temperatures are in the range of 100 to 250° C., preferably 110 to 220° C., more preferably 120 to 210° C., most preferably 130 to 200° C. The preferred dwell time at this temperature is preferably at least 10 minutes, more preferably at least 20 minutes, most preferably at least 30 minutes, and typically at most 60 minutes.

In a preferred embodiment of the present invention, the polymer particles are cooled after the surface postcrosslinking. The cooling is preferably performed in contact coolers, more preferably paddle coolers and most preferably disk coolers. Suitable coolers are, for example, Hosokawa Bepex® Horizontal Paddle Cooler (Hosokawa Micron GmbH; Leingarten; Germany), Hosokawa Bepex® Disk Cooler (Hosokawa Micron GmbH; Leingarten; Germany), Holo-Flite® coolers (Metso Minerals Industries Inc.; Danville; USA) and Nara Paddle Cooler (NARA Machinery Europe; Frechen; Germany). Moreover, fluidized bed coolers may also be used.

In the cooler, the polymer particles are cooled to preferably 40 to 90° C., more preferably 45 to 80° C., most preferably 50 to 70° C.

Subsequently, the surface postcrosslinked polymer particles can be classified again, with excessively small and/or excessively large polymer particles being removed and recycled into the process.

To further improve the properties, the surface postcrosslinked polymer particles can be coated or remoisturized.

The remoisturizing is preferably performed at 40 to 120° C., more preferably at 50 to 110° C., most preferably at 60 to 100° C. At excessively low temperatures the polymer particles tend to form lumps, and at higher temperatures water already evaporates to a noticeable degree. The amount of water used for remoisturizing is preferably from 1% to 10% by weight, more preferably from 2% to 8% by weight and most preferably from 3% to 5% by weight. The remoisturizing increases the mechanical stability of the polymer particles and reduces their tendency to static charging. The remoisturizing is advantageously performed in a cooler after the thermal surface postcrosslinking.

Suitable coatings for improving the swell rate and the gel bed permeability (GBP) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20. Suitable coatings for dust binding, for reducing the tendency to caking and for increasing the mechanical stability are polymer dispersions as described in EP 0 703 265 B1, and waxes as described in U.S. Pat. No. 5,840,321.

Subsequently, the coated and/or remoisturized polymer particles can be classified again, with removal of excessively small and/or excessively large polymer particles and recycling into the process.

The present invention further provides hygiene articles comprising superabsorbents produced by the process of the invention.

EXAMPLES

The examples were calculated by means of industrial standard simulation programs.

Example 1

In a continuous preneutralization, 5715 kg/h (79.3 kmol/h) of acrylic acid, 3635 kg/h (45.4 kmol/h) of 50% by weight sodium hydroxide solution and 5650 kg/h of water are mixed and cooled to 30° C. by means of a shell and tube heat exchanger. 85% of the cooled mixture is recycled into the preneutralization. The neutralization level is 57.3 mol %. The solids content is 44.8% by weight. The dwell time of the monomer solution in the preneutralization is about one hour.

A shell and tube heat exchanger is used to heat 15 000 kg/h of the preneutralized monomer solution in countercurrent. The shell and tube heat exchanger has an internal surface area of 35 m$^2$. The temperature of the heating medium (feed temperature) is 100° C. (condensate). The heating medium flow rate is 12 100 kg/h. The temperature of the heating medium at the heat exchanger outlet is 60° C. The heating output of the heat exchanger is 562 kW. The temperature of the monomer solution rises to 75° C. The dwell time of the monomer solution in the shell and tube heat exchanger is about 2.5 minutes.

The heated monomer solution is postneutralized with 1123 kg/h (14.0 kmol/h) of 50% by weight sodium hydroxide solution. The temperature of the sodium hydroxide solution is 40° C. The heat of neutralization raises the temperature to 95° C. The neutralization level is 75.0 mol %. The solids content is 43.6% by weight. The dwell time of the monomer solution in the postneutralization is about 12 seconds.

Subsequently, crosslinker and initiator are added successively to the postneutralized monomer solution, and the monomer solution is transferred into a polymerization reactor and polymerized.

Example 2 (Comparative Example)

In a continuous preneutralization, 5715 kg/h (79.3 kmol/h) of acrylic acid, 3635 kg/h (45.4 kmol/h) of 50% by weight sodium hydroxide solution and 5650 kg/h of water are mixed and cooled to 30° C. by means of a shell and tube heat exchanger. 85% of the cooled mixture is recycled into the preneutralization. The neutralization level is 57.3 mol %. The solids content is 44.8% by weight. The dwell time of the monomer solution in the preneutralization is about one hour.

15 000 kg/h of the preneutralized monomer solution is postneutralized with 1123 kg/h (14.0 kmol/h) of 50% by weight sodium hydroxide solution. The temperature of the sodium hydroxide solution is 40° C. The heat of neutralization raises the temperature to 53.4° C. The neutralization level is 75.0 mol %. The solids content is 43.6% by weight. The dwell time of the monomer solution in the postneutralization is about 12 seconds.

A shell and tube heat exchanger is used to heat the postneutralized monomer solution. The shell and tube heat exchanger has an internal surface area of 35 m$^2$. The temperature of the heating medium (feed temperature) is 100° C. (condensate). The heating medium flow rate is 12 100 kg/h. The temperature of the heating medium at the heat exchanger outlet is 73°C. The heating output of the heat exchanger is 378 kW. The temperature of the monomer solution rises to 83.7°C. The dwell time of the monomer solution in the shell and tube heat exchanger is about 2.5 minutes.

Subsequently, crosslinker and initiator are added successively to the heated monomer solution, and the monomer solution is transferred into a polymerization reactor and polymerized.

Example 3 (Comparative Example)

In a continuous preneutralization, 5715 kg/h (79.3 kmol/h) of acrylic acid, 3635 kg/h (45.4 kmol/h) of 50% by weight sodium hydroxide solution and 5650 kg/h of water are mixed and cooled to 30° C. by means of a shell and tube heat exchanger. 85% of the cooled mixture is recycled into the preneutralization. The neutralization level is 57.3 mol %. The solids content is 44.8% by weight. The dwell time of the monomer solution in the preneutralization is about one hour.

15 000 kg/h of the preneutralized monomer solution is postneutralized with 1123 kg/h (14.0 kmol/h) of 50% by weight sodium hydroxide solution. The temperature of the sodium hydroxide solution is 40° C. The heat of neutralization raises the temperature to 53.4° C. The neutralization level is 75.0 mol %. The solids content is 43.6% by weight. The dwell time of the monomer solution in the postneutralization is about 12 seconds.

A shell and tube heat exchanger is used to heat the postneutralized monomer solution. The shell and tube heat exchanger has an internal surface area of 35 m$^2$. The temperature of the heating medium (feed temperature) is 111° C. (1.5 bar heating steam). The heating medium flow rate is 897 kg/h. The temperature of the heating medium at the heat exchanger outlet is 60° C. The heating output of the heat exchanger is 520 kW. The temperature of the monomer solution rises to 95° C. The dwell time of the monomer solution in the shell and tube heat exchanger is about 2.5 minutes.

Subsequently, crosslinker and initiator are added successively to the heated monomer solution, and the monomer solution is transferred into a polymerization reactor and polymerized.

Example 4

In a continuous preneutralization, 5715 kg/h (79.3 kmol/h) of acrylic acid, 3635 kg/h (45.4 kmol/h) of 50% by weight sodium hydroxide solution and 5650 kg/h of water are mixed and cooled to 30° C. by means of a shell and tube heat exchanger. 85% of the cooled mixture is recycled into the preneutralization. The neutralization level is 57.3 mol %. The solids content is 44.8% by weight. The dwell time of the monomer solution in the preneutralization is about one hour.

A shell and tube heat exchanger is used to heat 15 000 kg/h of the preneutralized monomer solution in countercurrent. The shell and tube heat exchanger has an internal surface area of 9.4 m$^2$. The temperature of the heating medium (feed temperature) is 150° C. (4.8 bar heating steam). The heating medium flow rate is 960 kg/h. The temperature of the heating medium at the heat exchanger outlet is 60° C. The heating output of the heat exchanger is 562 kW. The temperature of the monomer solution rises to 75° C. The dwell time of the monomer solution in the shell and tube heat exchanger is about 40 seconds.

The heated monomer solution is postneutralized with 1123 kg/h (14.0 kmol/h) of 50% by weight sodium hydroxide solution. The temperature of the sodium hydroxide solution is 40° C. The heat of neutralization raises the temperature to 95° C. The neutralization level is 75.0 mol %. The solids content is 43.6% by weight. The dwell time of the monomer solution in the postneutralization is about 12 seconds.

Subsequently, crosslinker and initiator are added successively to the postneutralized monomer solution, and the monomer solution is transferred into a polymerization reactor and polymerized.

Example 5 (Comparative Example)

In a continuous preneutralization, 5715 kg/h (79.3 kmol/h) of acrylic acid, 3635 kg/h (45.4 kmol/h) of 50% by weight sodium hydroxide solution and 5650 kg/h of water are mixed and cooled to 30° C. by means of a shell and tube heat exchanger. 85% of the cooled mixture is recycled into the preneutralization. The neutralization level is 57.3 mol %. The solids content is 44.8% by weight. The dwell time of the monomer solution in the preneutralization is about one hour.

15 000 kg/h of the preneutralized monomer solution is postneutralized with 1123 kg/h (14.0 kmol/h) of 50% by weight sodium hydroxide solution. The temperature of the sodium hydroxide solution is 40° C. The heat of neutralization raises the temperature to 53.4° C. The neutralization level is 75.0 mol %. The solids content is 43.6% by weight. The dwell time of the monomer solution in the postneutralization is about 12 seconds.

A shell and tube heat exchanger is used to heat the postneutralized monomer solution. The shell and tube heat exchanger has an internal surface area of 9.4 m$^2$. The temperature of the heating medium (feed temperature) is 150° C. (4.8 bar heating steam). The heating medium flow rate is 960 kg/h. The temperature of the heating medium at the heat exchanger outlet is 60° C. The heating output of the heat exchanger is 446 KW. The temperature of the monomer solution rises to 89° C. The dwell time of the monomer solution in the shell and tube heat exchanger is about 40 seconds.

Subsequently, crosslinker and initiator are added successively to the heated monomer solution, and the monomer solution is transferred into a polymerization reactor and polymerized.

Example 6 (Comparative Example)

In a continuous preneutralization, 5715 kg/h (79.3 kmol/h) of acrylic acid, 3635 kg/h (45.4 kmol/h) of 50% by weight sodium hydroxide solution and 5650 kg/h of water are mixed and cooled to 30° C. by means of a shell and tube heat exchanger. 85% of the cooled mixture is recycled into the preneutralization. The neutralization level is 57.3 mol %. The solids content is 44.8% by weight. The dwell time of the monomer solution in the preneutralization is about one hour.

15 000 kg/h of the preneutralized monomer solution is postneutralized with 1123 kg/h (14.0 kmol/h) of 50% by weight sodium hydroxide solution. The temperature of the sodium hydroxide solution is 40° C. The heat of neutralization raises the temperature to 53.4° C. The neutralization level is 75.0 mol %. The solids content is 43.6% by weight. The dwell time of the monomer solution in the postneutralization is about 12 seconds.

A shell and tube heat exchanger is used to heat the postneutralized monomer solution. The shell and tube heat exchanger has an internal surface area of 9.4 m$^2$. The temperature of the heating medium (feed temperature) is 165° C. (7 bar heating steam). The heating medium flow rate is 920 kg/h. The temperature of the heating medium at the heat exchanger outlet is 60° C. The heating output of the heat exchanger is 520 kW. The temperature of the monomer solution rises to 95° C. The dwell time of the monomer solution in the shell and tube heat exchanger is about 40 seconds.

Subsequently, crosslinker and initiator are added successively to the heated monomer solution, and the monomer solution is transferred into a polymerization reactor and polymerized.

The examples show that the process of the invention enables lower feed temperatures in the heat exchanger. But higher feed temperatures increase the soiling of the heat exchanger by polymer deposits. Moreover, as a result, the process of the invention lowers the dwell time at relatively high temperatures.

The invention claimed is:

1. A process for producing superabsorbent particles by polymerizing a monomer solution or suspension comprising
   a) at least one ethylenically unsaturated monomer which bears an acid group and is at least partly neutralized,
   b) at least one crosslinker,
   c) at least one initiator,
   d) optionally one or more ethylenically unsaturated monomer copolymerizable with the monomer mentioned under a), and
   e) optionally one or more water-soluble polymer, comprising
   i) continuously preneutralizing the monomer while cooling and partly recycling the preneutralized monomer into the preneutralization,
   ii) continuously heating the preneutralized monomer from step i) by means of a heat exchanger,
   iii) continuously postneutralizing the heated monomer from step ii),
   iv) adding the crosslinker to the monomer solution from step iii), and
   v) adding the initiator to the monomer solution from step iv), wherein the monomer solution or suspension is at a temperature of 70 to 99° C. prior to entry into a polymerization reactor and a temperature of a heating medium used in the heat exchanger in step ii) is less than 160° C.

2. The process according to claim 1, wherein the preneutralized monomer is cooled in step i) to a temperature of less than 45° C.

3. The process according to claim 1, wherein the preneutralized monomer is cooled in step i) to a temperature of less than 40° C.

4. The process according to claim 1, wherein the preneutralized monomer is cooled in step i) to a temperature of less than 35° C.

5. The process according to claim 1, wherein between 40% and 98% of the preneutralized monomer is recycled into step i).

6. The process according to claim 1, wherein between 60% and 95% of the preneutralized monomer is recycled into step i).

7. The process according to claim 1, wherein between 80% and 90% of the preneutralized monomer is recycled into step i).

8. The process according to claim 1, wherein the temperature of the heating medium used in the heat exchanger in step ii) is less than 140° C.

9. The process according to claim 1, wherein the temperature of the heating medium used in the heat exchanger in step ii) is less than 120° C.

10. The process according to claim 1, wherein the temperature of the heating medium used in the heat exchanger in step ii) is less than 110° C.

11. The process according to claim 1, wherein the neutralization level is increased in step ii) by 5 to 45 mol %.

12. The process according to claim 1, wherein the neutralization level is increased in step ii) by 10 to 35 mol %.

13. The process according to claim 1, wherein the neutralization level is increased in step ii) by 15 to 25 mol %.

14. The process according to claim 1, wherein monomer a) is acrylic acid.

15. The process according to claim 1, wherein the superabsorbent particles are surface postcrosslinked.

* * * * *